(12) United States Patent
Dupuis et al.

(10) Patent No.: US 8,087,498 B2
(45) Date of Patent: Jan. 3, 2012

(54) HIGH POWER/WEIGHT RATIO BRAKING DEVICE BASED ON SHAPE MEMORY MATERIAL TECHNOLOGY

(75) Inventors: Daniel Dupuis, Neuville (CA);
Stephane Bedard, Saint-Augustin-de-Desmaures (CA);
Pierre-Olivier Roy, Sainte-Foy (CA)

(73) Assignee: Victhom Human Bionics Inc., Saint-Augustin-de-Desmaures, Quebec (CA)

( * ) Notice: Subject to any disclaimer, the term of this patent is extended or adjusted under 35 U.S.C. 154(b) by 700 days.

(21) Appl. No.: 10/553,579

(22) PCT Filed: Apr. 19, 2004

(86) PCT No.: PCT/CA2004/000590
§ 371 (c)(1),
(2), (4) Date: Apr. 20, 2006

(87) PCT Pub. No.: WO2004/092606
PCT Pub. Date: Oct. 28, 2004

(65) Prior Publication Data
US 2006/0201757 A1 Sep. 14, 2006

(51) Int. Cl.
*F16D 63/00* (2006.01)
(52) U.S. Cl. .................. 188/68; 188/156; 188/65.3
(58) Field of Classification Search .......... 188/67–69, 188/64, 65.1–65.5, 156–158, 162; 623/43
See application file for complete search history.

(56) References Cited

U.S. PATENT DOCUMENTS

| 3,557,387 | A | | 1/1971 | Ohlenbusch et al. |
| 4,792,338 | A | | 12/1988 | Rennerfelt |
| 4,932,210 | A | | 6/1990 | Julien et al. |
| 5,749,533 | A | * | 5/1998 | Daniels .................. 242/287 |
| 5,831,417 | A | * | 11/1998 | Chu ................... 322/1 |
| 6,045,076 | A | * | 4/2000 | Daniels ............... 242/287 |
| 6,286,635 | B1 | | 9/2001 | Tamor |

FOREIGN PATENT DOCUMENTS

| DE | 4016146 C | | 8/1991 |
| JP | 63130935 A | * | 6/1988 |
| JP | 2310856 A | | 12/1990 |
| JP | 3037433 A | | 2/1991 |
| WO | WO94/09727 A | | 5/1994 |

* cited by examiner

*Primary Examiner* — Xuan Lan Nguyen
(74) *Attorney, Agent, or Firm* — Knobbe, Martens, Olson & Bear LLP

(57) ABSTRACT

The braking device is provided a set of shape memory alloy activators positioned, in an agonistic-antagonistic configuration on each side of a brake lever. Braking and releasing phases are dictated by the austenitic transformation of the shape memory alloy activators. During brake activation, shrinking of the braking activator brings the friction pad in contact with a rotating drum creating a braking friction torque. Once the brake has been activated, deformation of a flexible fiberglass component prevents brake releasing by applying sufficient normal force between the drum and the friction pad. Conversely, upon heating of the releasing activator, the pad looses its grip and the drum is free to rotate.

25 Claims, 9 Drawing Sheets

HIGH POWER/WEIGHT RATIO BRAKING DEVICE BASED ON SHAPE MEMORY MATERIAL TECHNOLOGY

The invention relates to brakes.

When it comes to slowing down or completely stopping the rotation of a mechanical system, different braking strategies are being used. The most common brake technologies include viscous brakes, hydrodynamic brakes where a fluid is forced to pass through a flow restriction orifice, magnetorheological brakes where a particular fluid changes its viscosity under the application of a variable magnetic field, electromagnetic brakes where a force opposing the rotation of a system is set up by inducing eddy currents within a metal disc inserted between two electromagnets, and friction brakes where two surfaces are pressed one against the other.

The are many types of friction brakes, which are set apart by the shape of their friction surfaces and the nature of their activation principle. There are six main types of friction brakes, namely drum brakes, disc brakes, belt brakes, electromechanical and electromechanical power off brakes and magnetic particles brakes. Drum brakes consists of a cylindrical braking surface on to which one or more brake shoes are pressed when the brakes are activated. Friction of the shoe on the drum surface slows down the rotation of the system. Disc brakes use a clamping action to produce friction between a disc and two pads mounted in a caliper. As the caliper pinches the disc with the pads, which are positioned on opposite sides of the disc, the rotation of the system is slowed down. Belt brakes consist of a friction belt wrapped around a drum. The tension in the belt is proportional to the gripping force between the belt and drum, thus increasing this tension slows down the rotation of the drum. All these friction brakes may either be hydraulically, pneumatically or electrically activated as long as the selected activation principle ensures adequate functioning of the mobile brake element (shoe, pads or belt).

Electromechanical brakes operate via an electric actuation, but transmit torque mechanically. When voltage is applied to the brake, a coil is energized creating a magnetic field, which turns the coil into an electromagnet. The resulting magnetic flux attracts an armature that is brought into contact with friction pads. Since the armature is fixed relative to the shaft and the pads are fixed relative to the frame, activation of the brake slows down the rotation of the system. In most designs, springs hold the armature away from the brake surface when power is released. Conversely, in some designs, a series of springs force the armature in contact with the brake surface when no power is applied to it. These brakes, called electromechanical power off brakes, are released by applying voltage to a coil, which pushes the armature away from the brake surface.

In magnetic particle brakes, magnetic particles are located in a cavity where they simply lay when no power is applied. However, as soon as voltage is applied to a coil located on top of the cavity, the magnetic flux created tends to bind the particles together. As the voltage is increased, binding of the particles becomes stronger. Since the brake rotor passes through these bounded particles, the resistance force created on the rotor slows down the rotation of the system.

In the field of prosthetics, several types of brakes have been used in the past to control relative pivotal movement between components of the prosthesis, each having their benefits and drawbacks.

Viscous brakes are well suited for prosthetic applications but are subject to leakage and failure under high loading conditions. Moreover, their relatively high weight makes them less interesting compared to other solutions.

Magnetorheological fluids are theoretically suitable for applications where the viscosity of the braking device needs to be rapidly and accurately modified. However, practical applications have shown that this change in viscosity is not rapid and accurate enough to achieve acceptable performances in the field of prosthetics. Moreover, as with the viscous brakes, their relatively high weight is detrimental to their selection in applications where dynamic braking is not a requirement.

Friction brakes are not recommended for dynamic braking applications since the friction coefficient of the contact surfaces tends to change after extended use. However, their simplicity, compactness and lightness make them an interesting choice whenever dynamic braking is not necessary.

Furthermore, all braking devices presented above have a common imitation in that they require power to remain activated or inactivated.

Accordingly, it is an object of the present application to obviate or mitigate some or all of the above disadvantages.

SUMMARY

According to one aspect of the present invention, there is provided a friction brake assembly to act between a first component and a second component relatively moveable with respect to the first component and comprising a brake member connected to the first component, a carrier connected to the second component and a friction pad attached to the carrier for engagement with the brake member. A first actuator including at least one shape memory alloy element is operable upon the carrier to move the friction pad into engagement with the brake member. A second actuator including at least one shape memory alloy element is operable upon the carrier to move the friction pad away from the brake member. A controller operates selectively on the first and second actuators.

According to a further aspect of the present invention, there is provided a prosthesis having a pair of limbs pivotally connected on one another by a mechanical joint. An actuator is connected between the limbs to effect relative rotation there between and a friction brake assembly as described above acts to inhibit such relative motion. The friction brake assembly is operative upon the actuator to inhibit further movement in the joint.

The braking device exhibits the ability to maintain a given state of activation when no power is supplied to it. The preferred embodiment of this device takes advantage of some particular characteristic of shape memory alloys (SMA), namely the shape memory effect. The preferred embodiment of brake may be packaged on a leg prosthesis for above knee amputees but is not restricted to this specific application. It suits any general application where a braking action needs to be applied between a pair of components.

In the preferred embodiment; actuation of the brake is provided a set of shape memory alloy (SMA) wires positioned, in an agonistic-antagonistic configuration on each side of a brake lever. Braking and releasing phases are dictated by the austenitic transformation of the SMA wires by the application of an electrical current to shorten one set of wires. During brake activation, shrinking of the braking wires brings the friction pad in contact with a rotating drum creating a braking friction torque. Once the brake has been activated, deformation of a flexible component prevents the releasing of the brake by maintaining sufficient normal force between the drum and the friction pad. Conversely, upon activation of the releasing wires, the pad looses its grip and the drum is free to rotate.

Half of the SMA wires are used for brake activation while the other half is used for brake release. Braking amplification factor is determined by the position of the lever pivot. Aluminum 6061-T6 is well suited as a bulk material for weight reduction purposes. In order to increase the brake coefficient of friction, aluminum-bronze and steel are used for braking pad and drum manufacturing respectively. It is estimated that a 5V-50 A power supply is suitable for brake activation and release according to the SMA specifications.

Other features and advantages of the present invention will be more readily apparent from the following detailed description, which proceeds with reference to the accompanying figures.

The braking system has been developed in the context of a prosthesis for an above knee amputee and therefore will be described within that context to illustrate the particular attributes of the system to this field of endeavor. However, it will be understood that the braking system is more generally applicable.

Figure 1:
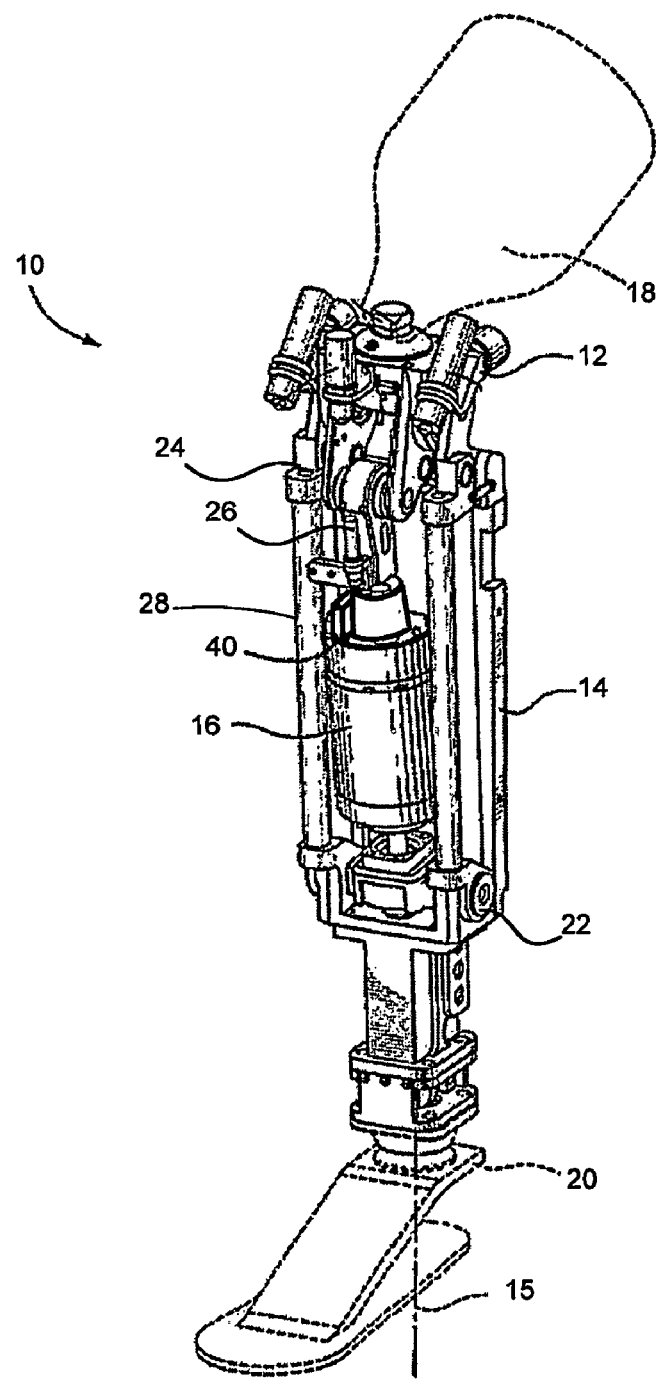
FIG. 1 is a perspective view of a prosthesis incorporating a braking system.
Figure 3:
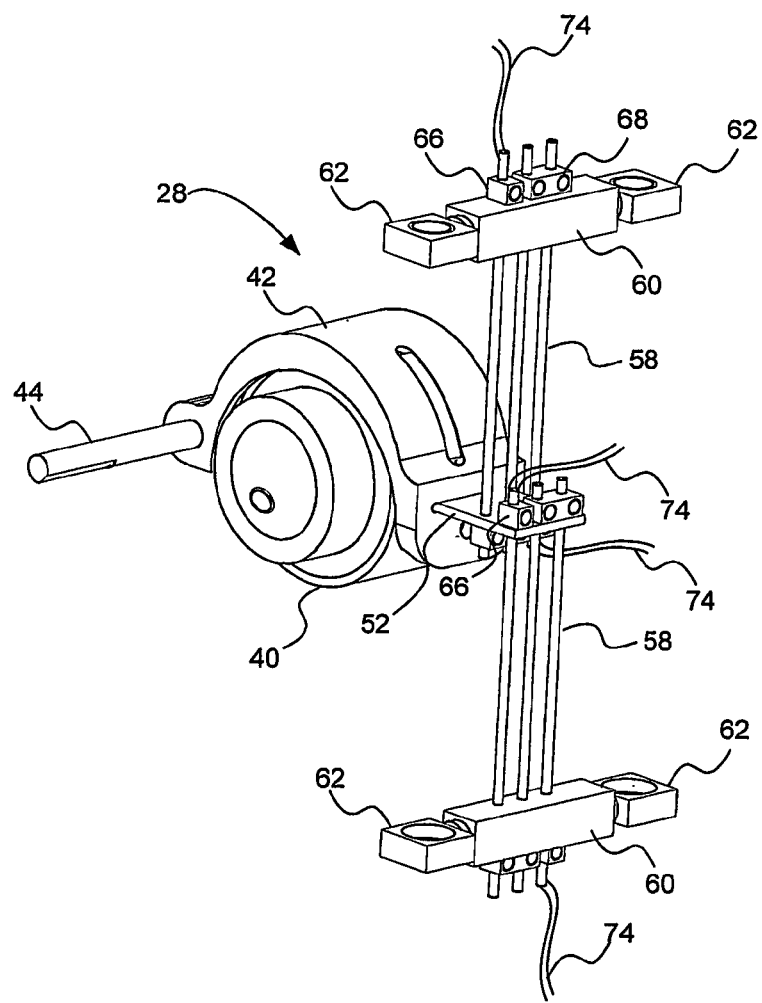
FIG. 3 is a further perspective view of the assembled components of the braking system shown in FIG. 2.
Figure 4:
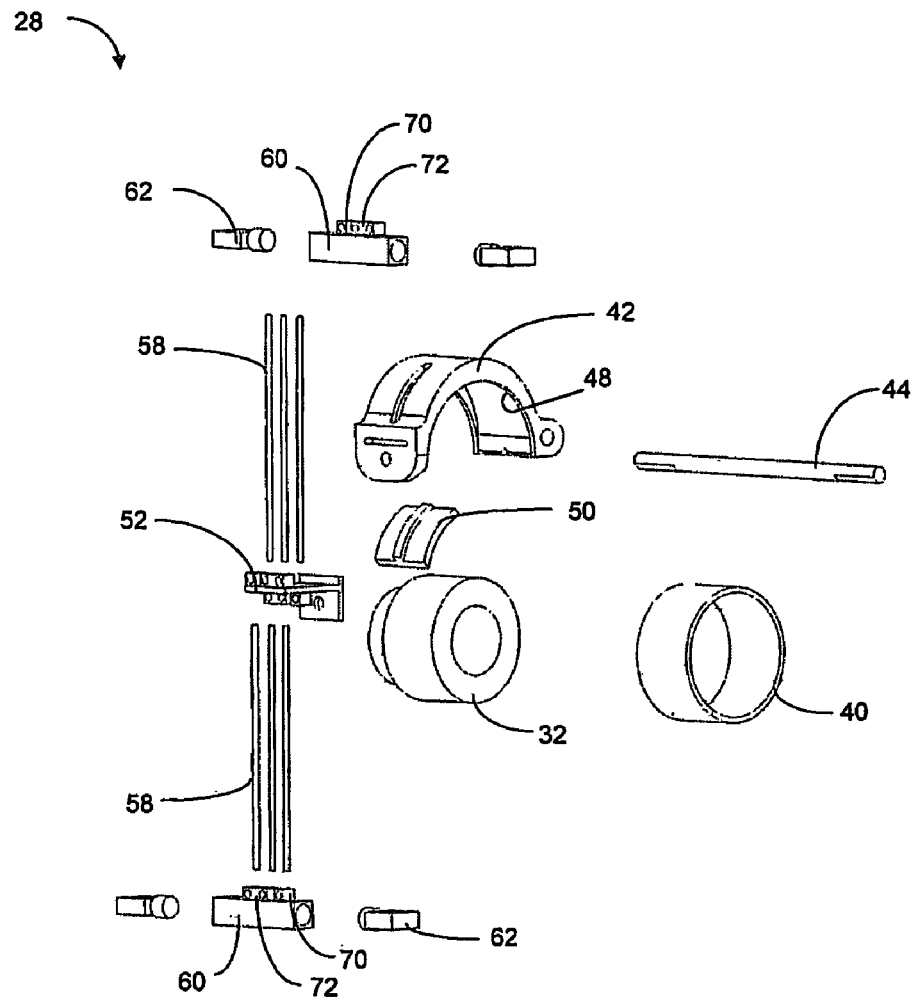
FIG. 4 is an exploded view of the components of the braking system shown in FIG. 1.

Referring therefore to FIG. 1, a powered prosthesis 10 has, a knee joint assembly 12 connected between a lower limb 14 and a socket 18. The knee joint assembly 12 permits relative rotation between the socket 18 and the lower limb 14 which in turn is connected to a foot 15 through a cantilevered support beam 20. Rotation of the knee joint 12 is controlled by an actuator 16 pivotally connected, as indicated at 22, to the lower limb assembly 14 and at its opposite end to bifurcated arms 24 forming part of the knee joint assembly 12. The actuator 16 is a screw type actuator with an armature rotatable within the outer casing and engaged through a screw thread with a linearly displaceable output shaft 26. Rotation of the armature induces longitudinal displacement of the shaft 26 causing the actuator 16 to lengthen or shorten and cause a corresponding rotation in the knee joint assembly 12. Further details of the actuator and knee joint assembly may be found from the Applicants corresponding PCT Application PCT/CA2003/00092 and accordingly further description is not required at this time. In order to inhibit rotation of the knee joint assembly 12, a brake assembly 28 is incorporated on the actuator 16 and is operable to inhibit changes in the length of the actuator 16 when engaged. The details of the brake assembly 28 are more readily seen in FIGS. 2, 3 and 4.

Figure 2:
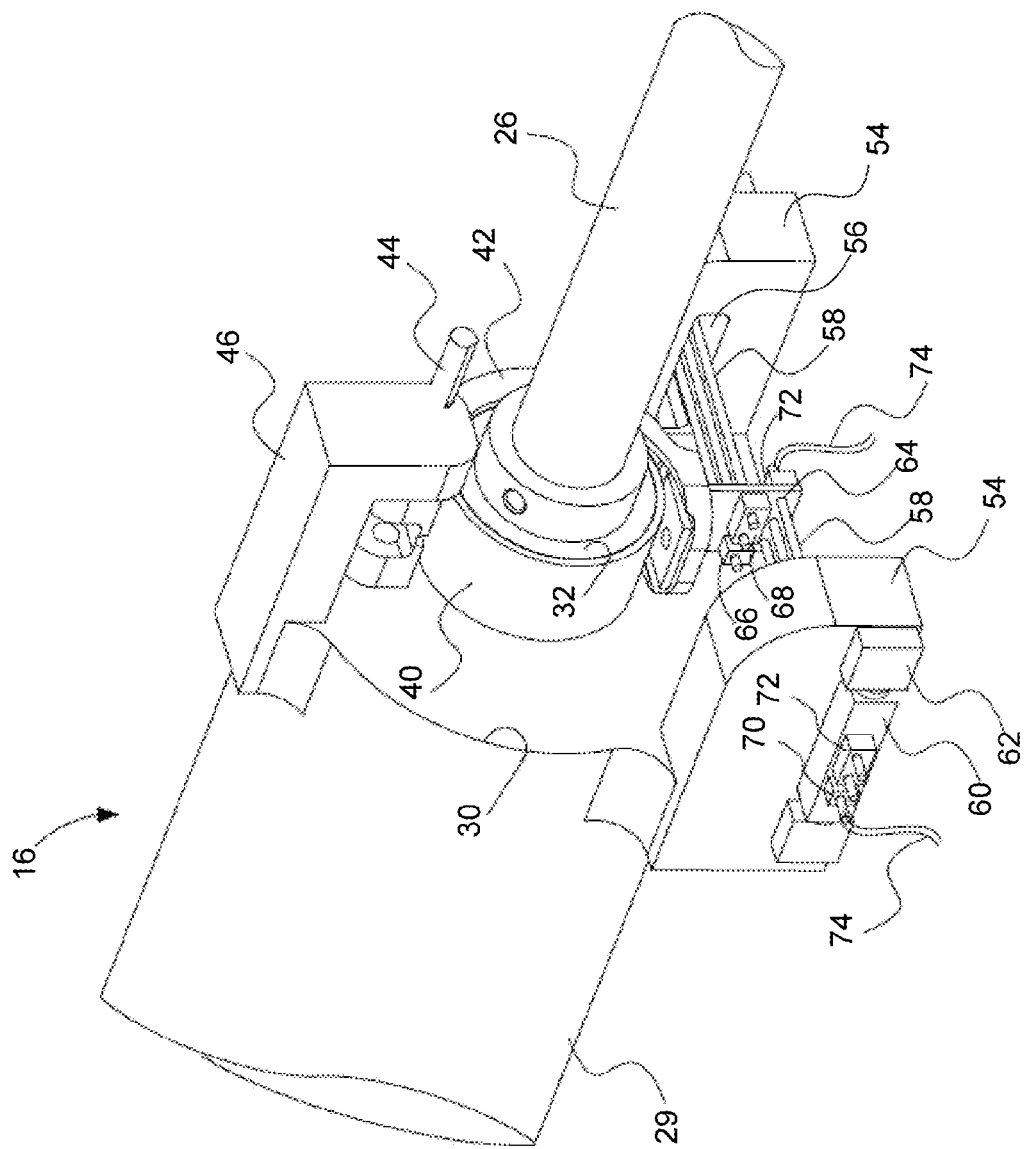
FIG. 2 is a perspective view on an enlarged scale of the braking system utilized in FIG. 1.

Referring therefore to FIG. 2, the actuator 16 has an outer housing 29 with an end cap 30. An armature is rotatably mounted within the housing 29 and is rotatably supported in the end cap 30 on a boss 32 that projects through the end cap 30. The actuator shaft 26 extends through the boss 32 and is displaceable longitudinally upon rotation of the armature by virtue of the screw threaded connection between the armature and the shaft 26. Rotation of the shaft 26 is inhibited by its connection to the ears 54.

The boss 32 has a brake drum 40 secured to it for rotation with the boss 32. A brake shoe carrier 42 is pivotally connected through a pin 44 to a mounting block 46 that projects from the body 29 of actuator 16. The carrier 42 acts as a lever and is formed as a semi-cylindrical cup having outer flanges 48 between which is secured a part cylindrical brake shoe 50. The brake shoe 50 is configured to conform to the outer surface of the brake drum 40 and frictionally engage the brake drum.

The opposite end of the carrier 42 to the pin 44 is connected to a beam 52 that projects radially between a pair of ears 54. The beam 52 is made from electronically non-conductive material and is designed to provide a controlled flexure upon application of a braking force as will be described below.

The ears 54 are secured to the body 28 of the actuator 16 and project axially to the extent of the brake assembly 28. Each of the ears 54 has an axial slot 56 to accommodate a set of shape memory alloy (SMA) rods 58. The rods are secured to a mounting block 60 which is pivotally secured by a trunnion 62 to the ears 54. The opposite ends of the rods 58 are received in respective sets of holes 64 formed in the beam 52. The rods 58 are secured to the beam 52 through terminal blocks 66, 68 which permits adjustment of the rods to ensure correct positioning of the shoe 50 relative to the drum 40.

The rods 58 are formed from a shape memory alloy, such as that available under the trademark Nitinol. The rods 58 are pre-stressed and shape memory alloy has the characteristic that a current applied to the rods 58 induces an austenitic transformation causing a shortening of the rods 58. Upon removal of the current, the length of the rods 58 remains unchanged until a further current is applied.

The rods 58 are secured to the mounting block 60 through terminal blocks 70, 72 in a manner similar to the terminal blocks 66, 68. The terminal block 70 engages a single rod 58 and has a conductor 74 connected to it. The terminal block 72 is connected to a pair of rods 58 and thus electrically connects the two rods to one another. The arrangement of blocks 70, 72 at both the ears 54 and the terminal blocks 66, 68 on beam 52 is such as to serially connect the rods 58 of each set in an electrical circuit and thereby ensure the same current is applied to each. The conductors 74 are connected to appropriate control circuit responsive to a control signal to apply or release the brake assembly 28.

In operation, the rods 58 are adjusted such that the carrier 42 maintains the shoe 50 in slight rubbing contact or minimal clearance with the drum 50 with no current supplied to the rods. In this condition, the actuator 16 is operable to rotate the armature and cause longitudinal displacement of the shaft 26 to effect rotation about the knee joint assembly. Rotation of the armature is controlled through suitable control functions as described in the above mentioned published PCT application.

When braking is required, rotation of the armature is inhibited to maintain the rod 26 in a fixed position by supplying a current through the conductor 74 to one of the sets of rods 58. The rods 58 of that set shorten upon application, upon passage of the current and thereby act through beam 52 to cause pivotal movement of the carrier 42 about the pin 44. This brings the shoe 50 into engagement with the outer surface of the drum 40 and applies a retarding force on the drum. The current supplied through the conductor 74 is terminated and the rods 58 maintain substantially their decreased length to hold the shoe in contact with the drum.

The application of force from the rods 58 through the beam 52 causes a flexure of the beam in proportion to the load applied. Upon removal of the current to the conductors 74, the deflection in the beam 52 is used as a bias to load the shoe 50 against the drum 40 through the intermediary of the carrier 42 and thereby maintain the braking force at the required level.

In order to release the brake, current is directed to the other set of rods 58 causing them to shorten and release the load on the carrier 42. Thus, by selectively applying the current to one or other of the set of rods, braking and release can be effected and the brake maintained in a stable position without the continued application of electrical power. During actuation, either to brake or release a current is supplied to one set of rods 58 but not the other. The force generated by the set to which current is supplied is much greater than that necessary to extend the other set over the limited range of motion required, ensuring effect actuation of the brake assembly 28.

In general, the brake assembly 28 may be adapted to any application where a braking torque needs to be either applied to or released from a mechanical system in rotation, even when no power is supplied to it. The brake requires power input only to change its state from activated to inactivated and vice-versa. The brake operation has been described by way of a particular embodiment describing an example application in which the brake assembly provides emergency braking on a motorized prosthesis in case of power failure and power shut down. The embodiment achieves this by taking advantage of some particular characteristic of shape memory alloys (SMA), namely the shape memory effect. A typical set of criteria to be fulfilled in this example application requires the brake to:

1. Be active at power failure or shut down, i.e. the brake remains in position after activation or release even if no power is supplied to it.
2. Withstand static load of the amputee when standing on one leg, i.e. the brake produces a minimal torque of 2.2 Nm when activated.
3. Completely blocks the prosthesis as quickly as possible, i.e. the brake blocks the prosthesis in less than 100 ms and may be released in less than 2 s.
4. Be electrically activated, i.e. the brake may be adapted to a commercially available power supply.
5. Respects specific security constraints, i.e. the brake operates in a temperature range defined between −20° C. and 40° C., the temperature of the SMA elements never exceeding 150° C. and brake lifespan is 100 000 cycles or better.
6. Respects specific mass and volume constraints, i.e. the brake, excluding the power supply, not weighing over 500 g and not exceeding the approximate volume of a 60 mm-diameter and 60 mm-long cylinder.

Using the general arrangement described above, the components may be dimensioned to meet these requirements in the context of a prosthesis. Suitable scaling may be applied to other environments.

Braking Drum

Drum rotational inertia is a major concern since it affects the dynamics of the prosthesis. In order to keep this parameter as low as possible, the boss 32 maximal diameter is fixed to 23 mm and the recommended material is aluminum 6061-T6. In order to improve the coefficient of friction between the boss 32 and the friction pad 50, a 1 mm-thick steel brake drum 40 is press-fitted onto the boss 32.

Friction Pad

In order to get high friction coefficient and high heat dissipation properties, aluminum-bronze is preferably used as raw material for the friction pad 50. Static coefficient of friction between aluminum-bronze and steel is estimated to 0.3. Considering this value and the short-shoe friction brake illustrated in FIG. 5 and defined by Equation 1, the normal force between the braking drum 32 and friction pad 50 needs to provide a 2.2 Nm braking torque on a 25 mm diameter drum is estimated to 587N.

$$N = \frac{T}{\mu r} \qquad \text{Equation 1}$$

Brake Lever

The brake amplification factor is directly related to the position of the lever pivot point. Considering the recommended stress applied to Nitinol© wires in martensitic state (20 MPa), the cross-sectional area A of those wires (0.78 mm²) and the normal force estimated above (587N), the amplification factor of the brake is evaluated to X=12.5.

Figure 5:
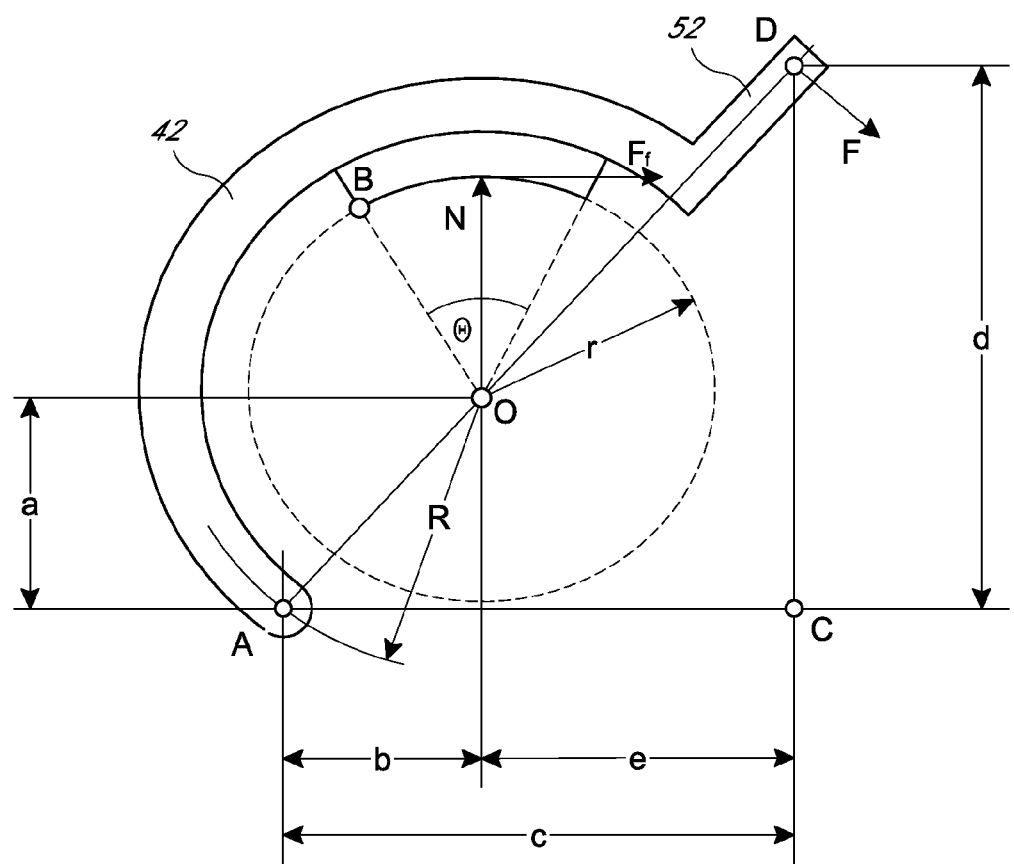
FIG. 5 is a free body diagram of the brake in an activated state.

Equation 2, Equation 3 and Equation 4 are obtained from FIG. 5. Substituting Equation 2 and Equation 3 in Equation 4 and solving for a, the position of the pivot point is estimated to a=13 mm and b=11 mm.

$$X = \frac{(c^2 + d^2)^{1/2}}{b - \mu(a+r)} \qquad \text{Equation 2}$$

$$L^2 = c^2 + d^2 \qquad \text{Equation 3}$$

$$R^2 = a^2 + b^2 \qquad \text{Equation 4}$$

For weight reduction purposes, aluminum 6061-T6 is recommended as the bulk material for the manufacturing of the carrier 42.

Beam

Figure 6:
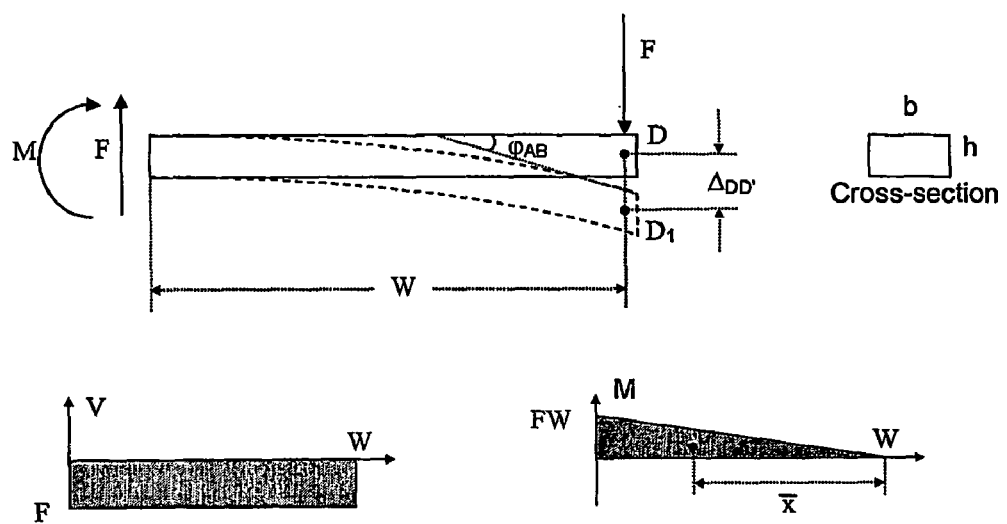
FIG. 6 is a deformation analysis of a component utilized in the brake shown in FIG. 2.

The beam 52 is made of a material which has a low Young's modulus/Tensile strength ratio, for example fiberglass such as S-Glass-Epoxy. From FIG. 6 and Equation 5 and considering the properties of this material (E=45 GPa and $S_u$=1000 MPa), a recommended flexural stress $\sigma_{max}$=300 MPa, a maximal force at the extremity of the beam 52 F=N/X=46.9N and a 10 mm-long and 10 mm-wide beam 52, the minimal beam thickness is estimated to $h_{min}$=1 mm. From FIG. 6 and Equation 6 and considering the same parameters, the deflection of the beam extremity is estimated to $\Delta_{DD1}$=0.42 mm.

$$h_{min} = \sqrt{\frac{6FW}{b\sigma_{max}}} \qquad \text{Equation 5}$$

$$\Delta_{DD_1} = \frac{4FW^3}{Ebh^3} \qquad \text{Equation 6}$$

SMA Elements

Figure 7:
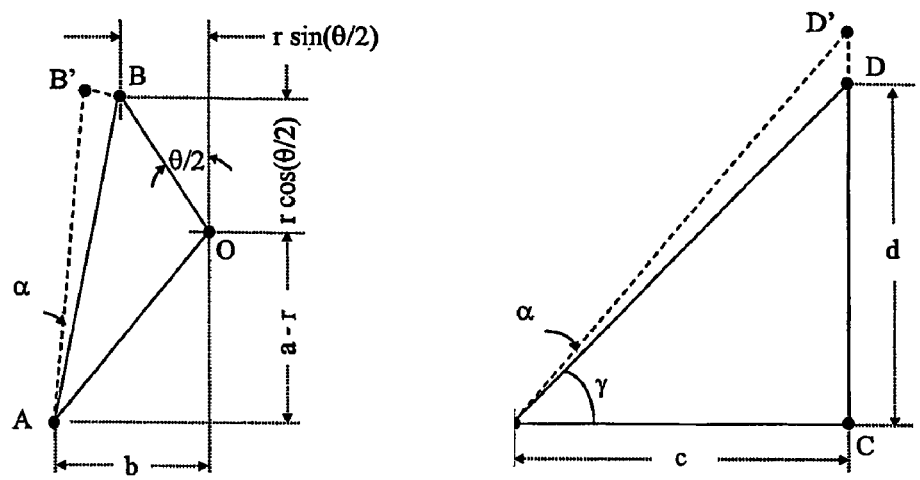
FIG. 7 is a trigometric analysis of a brake pad displacement for the brake shown in FIG. 2.

The length of the SMA elements (12, 21) may be obtained from Equation 7, where the active strain of the braking SMA elements (21) is $\epsilon_a$=4%, the elastic recovery strain of the releasing SMA elements (12), under the application of a force F=46.9N, is $\epsilon_{rec}$=0.07% while the strain of the braking SMA elements 58 under the same force is $\epsilon$=0.5%. Obtaining the displacement of brake carrier 42 extremity DD' from FIG. 7 and the deflection of the beam 52 extremity from Equation 6, the length of the SMA elements 58 is evaluated to be $L_{SMA}$=30 mm.

$$\epsilon_a L_{SMA} = DD' + \epsilon_{rec} L_{SMA} + \Delta_{DD1} + \epsilon L_{SMA} \quad \text{Equation 7}$$

Considering Equation 8, the volume of each SMA elements 58 is estimated to be V=23.4 mm³ (0.78 mm²×30 mm), that is the total volume of the three braking SMA elements 58 as well as the three releasing SMA elements 58 is $V_{TOT}$=70.2 mm³ (3×23.4 mm³). From Equation 9 and considering the density of Nitinol©, ρ=6450 kg/m³, the mass of each SMA elements 58 is estimated to be m=1.51×10⁻⁴ kg, that is the total mass of the three braking SMA elements 58 as well as the three releasing SMA elements 58 is $m_{TOT}$=4.53×10⁻⁴ kg (3×1.51×10⁻⁴ kg). Finally, from Equation 10 and considering the electrical resistivity of Nitinol©, $\rho_{el}$=0.8 μΩm and the three parallel SMA elements 58 on each side of the beam 52 connected in series via steel blocks 66, 68, 70, 72. The electrical resistance of SMA elements 58 is estimated to be $R_{el}$=0.092Ω.

$$V = AL \quad \text{Equation 8}$$

$$m = \rho V \quad \text{Equation 9}$$

$$R_{el} = \rho_{el} \frac{3L}{A} \quad \text{Equation 10}$$

Figure 8:
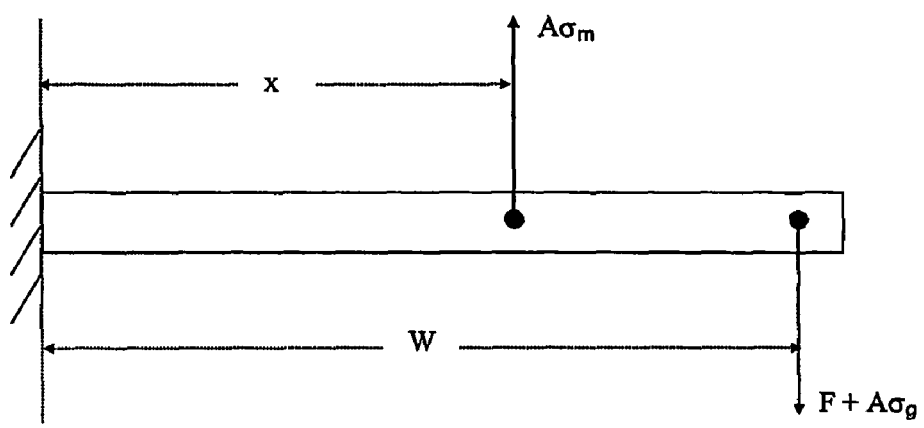
FIG. 8 is a free body diagram of the components shown in FIG. 6.

Stress generated by the braking SMA elements 58 during brake activation is obtained from FIG. 8 and Equation 11. Considering F=15.6N, W=10 mm, x=6 mm, A=0.78 mm² and $\sigma_m$=100 MPa, this parameter is estimated to be $\sigma_g$=80 MPa. From Equation 12 and considering room temperature, $T_{amb}$=25° C., Nitinol© transformation temperature, $A_s$=70° C., Nitinol© stress gradient dσ/dT=5 MPa/° C. and the value of $\sigma_g$ estimated above, total temperature elevation for brake activation is estimated to ΔT=61° C.

$$\sigma_g = \frac{FW + \sigma_m Ax}{AW} \quad \text{Equation 11}$$

$$\Delta T = \frac{1}{\sigma_g} \frac{d\sigma}{dT} + (A_s - T_{amb}) \quad \text{Equation 12}$$

Figure 9:
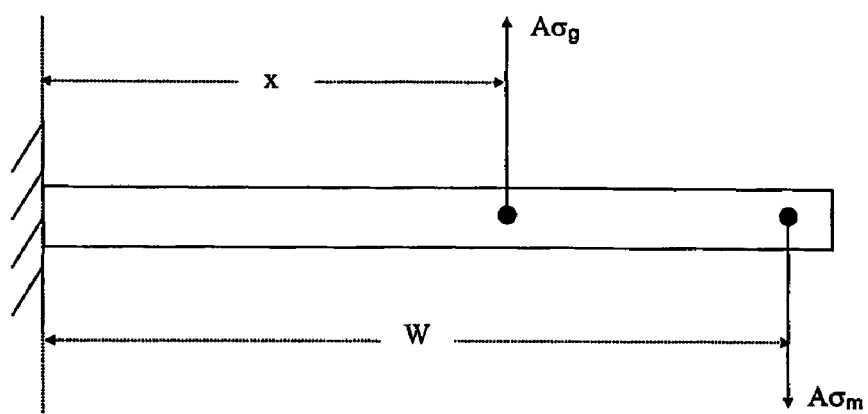
FIG. 9 is a free body diagram similar to FIG. 8 in a different mode of operation.

In a similar way, stress generated by the releasing SMA elements (12) during brake release is obtained from FIG. 9 and Equation 13. In this case, $\sigma_g$ is estimated to 167 MPa and the associated total SMA temperature elevation is estimated to ΔT=78° C.

$$\sigma_g = \frac{\sigma_m x}{W} \quad \text{Equation 13}$$

The energy required for brake activation or release is obtained from Equation 14. Considering the latent heat and transformation enthalpy of Nitinol©, $c_p$=322 J/kg° C. and $h_T$=24200 J/kg, the mass of material, m=4.53×10⁻⁴ kg and the temperature elevation values stated above, the energy associated with brake activation is, $U_{act}$=19.9 J, whereas the energy associated with brake release is, $U_{rel}$=22.3 J.

$$U = m(c_p \Delta T + h_T) \quad \text{Equation 14}$$

From Equation 15, considering the parameters evaluated above and the SMA brake functional requirements, the current required to activate the brake in less than 100 ms is estimated to $I_{act}$=46.5 A whereas the current required to release the brake in less than 2 s is estimated to $I_{rel}$=11 A. From Equation 16 and considering the current values evaluated above, the voltage associated with brake activation is estimated to $V_{act}$=4.3V whereas the voltage associated with brake release is estimated to $V_{rel}$=1V.

$$I = \sqrt{\frac{U}{Rt}} \quad \text{Equation 15}$$

$$V = RI \quad \text{Equation 16}$$

Frame

Components that remain fixed relative to the prosthesis, are considered part of the frame. Those components are: the SMA inserts 60, the trunnion blocks 62 and the lever pivot shaft 44. The SMA inserts 60 are made of, for example, HST II phenolic, a relatively rigid electrical insulator. The trunnion blocks are made, for example, of steel and are used to adjust the initial tension in the SMA elements 58. The lever pivot shaft 44 is made of, for example, steel and is positioned in such a way that the amplification factor of the brake is fixed to X=12.5.

Although the present invention has been described by way of a particular embodiment thereof, it should be noted that modifications may be applied to the present particular embodiment without departing from the scope of the present invention.

The embodiments of the invention in which an exclusive property or privilege is claimed are defined as follows:

1. A friction brake assembly to act between a main actuator and a linear shaft relatively moveable with respect to said main actuator, comprising:
   a linear shaft;
   a brake member connected to said linear shaft,
   a carrier connected to said main actuator;
   a friction pad attached to said carrier for removable engagement with said brake member;
   a first actuator comprising a plurality of shape memory alloy rods arranged in parallel, said first actuator being operatively coupled to said carrier and actuatable to move said friction pad into engagement with said brake member to apply a braking force on the brake member, wherein the engagement of said friction pad with said brake member inhibits movement of said linear shaft;
   a second actuator comprising a plurality of shape memory alloy rods arranged in parallel, said second actuator operatively coupled to said carrier and actuatable to move said friction pad away from said brake member to remove said braking force, wherein the moving away of said friction pad from said brake member allows movement of said linear shaft; and
   a control circuit to operate selectively said first and second actuator,
   wherein the first and second actuators are configured to change in length only when an electric current is applied thereto such that the length of the first and second actuators remains unchanged upon removal of the current, thereby allowing the friction pad and brake member to remain in a stable position without the continued application of electrical power to the first and second actuators.

2. The friction brake assembly of claim 1, wherein the linear shaft is configured to displace longitudinally with respect to the main actuator.

3. A friction brake assembly according to claim 1 wherein a resilient element is interposed between said first actuator and said carrier to maintain a bias against said brake member.

4. A friction brake assembly according to claim 3 wherein said resilient element is a beam projection from said carrier.

5. A friction brake assembly according to claim 1 wherein said shape memory alloy rods are tensile elements and said control circuit changes the length of said elements to actuate said brake.

6. A friction brake assembly according to claim 5 wherein said control circuit supplies an electrical current to respective ones of said elements to change the length thereof.

7. A friction brake assembly according to claim 1 wherein said brake member is a drum rotatably mounted on said main actuator and said carrier is pivotally secured to said first and second actuators for movement into or out of engagement with said drum.

8. A friction brake assembly according to claim 7 wherein said carrier includes a third member extending radially relative to said drum and said first and second actuators act between said linear shaft and said third member.

9. A friction brake assembly according to claim 8 wherein said third member is a flexible beam to couple resiliently said first and second actuators to said carrier.

10. A friction brake assembly according to claim 8 wherein said first and second actuators are tensile members formed from a shape memory alloy.

11. A friction brake assembly according to claim 10 wherein said tensile members are electrically connected in series and a current passing through said tensile members effects foreshortening of said tensile members.

12. A friction brake assembly according to claim 7 wherein said carrier is pivotally mounted for movement about an axis parallel to but spaced from the axis of rotation of said drum.

13. A prosthesis having a pair of limbs pivotally connected on one another by a mechanical joint, an actuator connected between said limbs to effect relative rotation there between and a friction brake assembly as claimed in claim 1 acting to inhibit such relative motion, said friction brake assembly being operative upon said actuator to inhibit further movement in said joint.

14. A prosthesis according to claim 13 wherein said actuator includes a pair of relatively displaceable components to change the length of said actuator and said friction brake assembly acts between said displaceable components.

15. A prosthesis according to claim 14 wherein said components are interconnected by a screw thread such that relative rotation there between causes a change in the length of said actuator and said friction brake assembly acts to inhibit relative rotation.

16. A prosthesis according to claim 13 wherein a resilient element is interposed between said first friction brake assembly actuator and said carrier to maintain a bias against said brake member.

17. A prosthesis according to claim 16 wherein said resilient element is a beam projection from said carrier.

18. A prosthesis according to claim 13 wherein said shape memory alloy rods are tensile elements and said controller changes the length of said elements to actuate said brake.

19. A prosthesis according to claim 18 wherein said controller supplies an electrical current to respective ones of said elements to change the length thereof.

20. A prosthesis according to claim 13 wherein said brake member is a drum rotatably mounted on said other member first component and said carrier is pivotally secured to said friction brake assembly actuators for movement into or out of engagement with said drum.

21. A prosthesis according to claim 20 wherein said carrier includes a member extending radially relative to said drum and said friction brake assembly actuators and act between spaced locations on said other member second component and said member, respectively.

22. A prosthesis according to claim 21 wherein said member is a flexible beam to couple resiliently said friction brake assembly actuators to said carrier.

23. A prosthesis according to claim 21 wherein said friction brake assembly actuators are tensile members formed from a shape memory alloy.

24. A prosthesis according to claim 23 wherein said tensile members are electrically connected in series and a current passing through said tensile members effects foreshortening of said tensile members.

25. A prosthesis according to claim 20 wherein said carrier is pivotally mounted for movement about an axis parallel to but spaced from the axis of rotation of said drum.

* * * * *

UNITED STATES PATENT AND TRADEMARK OFFICE
CERTIFICATE OF CORRECTION

PATENT NO. : 8,087,498 B2  
APPLICATION NO. : 10/553579  
DATED : January 3, 2012  
INVENTOR(S) : Daniel Dupuis et al.

Page 1 of 1

It is certified that error appears in the above-identified patent and that said Letters Patent is hereby corrected as shown below:

On Title Page 1, After (Item 65), Add "Related U.S. Application Data, (60) Provisional application No. 60/463,339, filed on April 17, 2003".
At Column 2, Line 19, Change "imitation" to --limitation--.
At Column 3, Line 29, Change "trigometric" to --trigonometric--.
At Column 5, Line 37, Change "2;" to --2.--.
At Column 5, Line 42, Change "2 s." to --2s.--.

Signed and Sealed this
Fourth Day of September, 2012

David J. Kappos
*Director of the United States Patent and Trademark Office*